United States Patent [19]

Mamadzhanov et al.

[11] 4,385,666
[45] May 31, 1983

[54] METHOD OF MAINTAINING PRESET PARAMETERS OF DRILLING MUD

[76] Inventors: Ulmas D. Mamadzhanov, 700000 Ts-1, dom 19, kv. 25; Vitold M. Bakhir, proezd Gaidara, 7-A, kv. 17; Stanislav A. Alekhin, Chilanzar, kvartal 24, 53, kv. 89, all of Tashkent, U.S.S.R.

[21] Appl. No.: 212,701
[22] PCT Filed: Sep. 28, 1979
[86] PCT No.: PCT/SU79/00088
§ 371 Date: Nov. 27, 1980
§ 102(e) Date: Nov. 3, 1980
[87] PCT Pub. No.: WO80/02038
PCT Pub. Date: Oct. 2, 1980

[30] Foreign Application Priority Data

Mar. 27, 1979 [SU] U.S.S.R. .................. 2736507

[51] Int. Cl.³ .............................................. E21B 21/06
[52] U.S. Cl. ........................................ 175/40; 73/151; 175/66; 175/206
[58] Field of Search ................. 175/40, 41, 50, 66, 175/206, 207; 166/250; 73/153, 155

[56] References Cited

U.S. PATENT DOCUMENTS

| | | | |
|---|---|---|---|
| 2,571,247 | 10/1951 | Huebotter | 175/66 X |
| 3,182,735 | 5/1965 | Salimbeni et al. | 175/50 |
| 3,711,765 | 1/1973 | Overton | 73/153 X |
| 3,722,606 | 3/1973 | Fertl et al. | 175/50 X |
| 3,893,522 | 7/1975 | Fertl et al. | 175/50 |

FOREIGN PATENT DOCUMENTS 169867 12/1962 U.S.S.R. .
672593 5/1979 U.S.S.R. .
746082 7/1980 U.S.S.R. .................. 175/206

OTHER PUBLICATIONS

Beits, R., "Opredelenie PH" by Khimiya Publishing House (Leningrad), 1968, pp. 366–372.
"Device for Rectification of Drilling Mud," WO80/02716, Dec. 1980.

*Primary Examiner*—Stephen J. Novosad
*Assistant Examiner*—George A. Suchfield
*Attorney, Agent, or Firm*—McAulay, Fields, Fisher, Goldstein & Nissen

[57] ABSTRACT

A method of maintaining preset parameters of a drilling mud delivered into a well in the process of drilling in which a value of the oxidation-reduction potential (redox potential) of the drilling mud is continuously measured at the inlet and outlet of the well. The obtained results are compared and a variation in the value of the redox potential of the drilling mud at the well outlet with respect to the value of the redox potential at the well inlet is registered. In case of any variation in the content of oxidation products in the drilling mud at the well outlet, the drilling mud is subjected to a unipolar electric treatment at the well inlet and the content of reduction reaction products in the drilling mud is increased until the preset value of the redox potential of the drilling mud is restored at the well outlet. In case of any variation in the content of reduction products in the drilling mud at the well outlet, the drilling mud is subjected to the unipolar electric treatment at the well inlet and the content of oxidation reaction products in the drilling mud is increased until the preset value of the redox potential is restored at the well outlet.

3 Claims, 2 Drawing Figures

METHOD OF MAINTAINING PRESET PARAMETERS OF DRILLING MUD

FIELD OF THE INVENTION

The present invention relates to the technique of preparing drilling muds for drilling wells and more particularly to the methods controlling and maintaining the properties and parameters of a drilling mud.

The present invention may be most suitably used in the oil and gas industry for drilling wells.

DESCRIPTION OF THE PRIOR ART

At present the preset parameters and properties of a drilling mud are maintained by chemical treatment of the original water-base mud suspension (E. G. Kister. Chemical Treatment of Drilling Muds, published 1972, Nedra Publishers, Moscow, p. 5-27, in Russian).

Known in the art also are methods of maintaining the properties and parameters of a drilling mud by introducing chemical agents into the drilling mud while it circulates in the well (E. G. Kister, Chemical Treatment of Drilling Muds, published 1972, Nedra Publishers, Moscow, pp. 34-98, in Russian).

However, the known methods suffer from a number of disadvantages which eventually lead to a decrease in the quality of a drilling mud and increase in costs drilling. All the known chemical agents when used with one definite purpose have unwanted side effects on other properties of the drilling mud, thus requiring the use of additional chemical agents. Practically, the use of almost all chemical agents is limited by the conditions of drilling, for example, by high temperatures and polymineral attack.

Another characteristic of known methods is the impossibility to repeatedly use expensive chemical agents which results in substantial expenses.

SUMMARY OF THE INVENTION

The invention is essentially aimed at the provision of a method of maintaining the preset parameters of a drilling mud, which will enable the mud parameters preset by the drilling schedule to be maintained throughout the entire drilling process.

The exact nature of the present invention resides a method of maintaining the preset parameters of a drilling mud delivered into a well in the drilling process, according to the invention a value of the oxidation-reduction potential (redox potential) of the drilling mud is continuously measured at the inlet and outlet of the well, the obtained values are compared, any variation in the value of the redox potential at the well outlet with respect to the value of the redox potential at the well inlet is registered, after which in case of any variation in the content of oxidation reaction products in the drilling mud at the well outlet, the drilling mud is subjected to a unipolar electric treatment at the well inlet and the content of reduction reaction products in the drilling mud is increased until the preset value of the redox potential of the drilling mud is restored at the well outlet, whereas in case of any variation in the content of reduction products in the drilling mud at the well outlet, the drilling mud is subjected to the unipolar electric treatment at the well inlet and the content of oxidation reaction products in the drilling mud is increased until the preset value of the redox potential of the drilling mud is restored at the well outlet.

The method of the invention makes it possible to increase the quality of a drilling mud and at the same time to reduce the cost of expensive chemical agents. In addition, the timely control of the drilling mud parameters continued until the preset parameters are restored makes it possible to prevent troubles and emergency conditions associated with the loss or blow-out of the drilling mud.

BRIEF DESCRIPTION OF THE DRAWINGS

The invention will now be described in detail with reference to the accompanying drawings illustrating a specific embodiment thereof, in which.

BEST MODE OF CARRYING OUT THE INVENTION

For a better understanding of the method described herein, certain aspects which form the basis of the present invention will be here explained.

In the most general form a drilling mud is essentially a heterogeneous liquid system containing solid phase particles, low-molecular ions and polyelectrolyte-polymers whose molecules include into their composition groups which are capable of ionizing in the drilling mud. The presence of these components in the drilling mud defines a number of the most important properties thereof from the standpoint of quality of the well drilling. Primarily, these properties should be referred to the capability of a drilling mud to exert a minimum physicochemical effect on the wall rocks and to cause the least disturbances, whenever possible, in the thermodynamic, chemical and physical process taking place at the "well-reservoir" interface. This basic condition predetermines the necessity for stability of the drilling mud (i.e. for maintaining all the characteristics thereof constant) in time under the action of high temperatures and aggressive salts.

Ion-exchange processes leading to oxidation-reduction reactions take place when the drilling mud circulating in a well comes in contact with the drilled rocks.

Any oxidation-reduction reaction proceeds according to the following pattern:

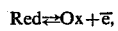

where: Red is the reducing agent, Ox is the oxidizing agent, e is the electron.

If an electrode made, for example, of platinum is immersed in a drilling mud, then an oxidation-reduction potential (further in the text referred to as a redox potential) occurs at the "electrode-drilling mud" interface. The value of the redox potential of a system serves as a measure of the intensity of the oxidation-reduction processes taking place in the given system and depends on the ratio of the concentrations in the system, of the oxidized and reduced ions which make up the given system.

Therefore, the stability of drilling muds may be determined by measuring the oxidation-reduction (redox) potential of the system, which characterizes the ratio of the oxidation and reduction components contained in the drilling mud.

The redox potential $\phi$ of a drilling mud having the activity of an oxidizing agent $a_{ox}$ and reducing agent $a_{red}$ is determined from the Nernst's equation:

$$\phi = \phi_o + \frac{RT}{ZF} \ln \frac{a_{ox}}{a_{red}},$$

where:

$\phi_o$ is the normal potential of electrode (platinum, gold);

$l_n$ is the natural logarithm;

R is the universal gas constant;

T is the temperature;

Z is the number of electrons participating in reaction;

F is the Faraday constant.

Figure 1:
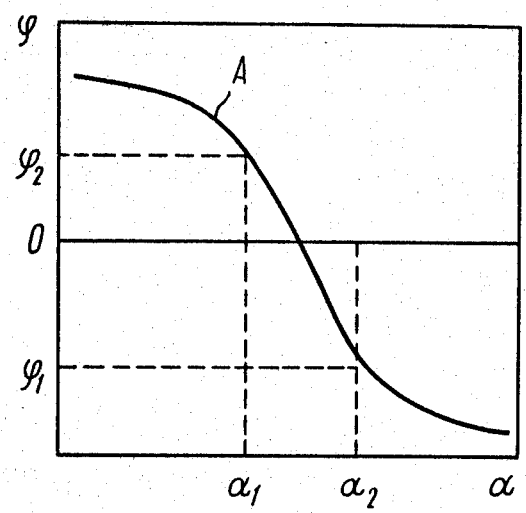
FIG. 1 illustrates a graph of the redox potential versus the relationship of activity between oxidation and reduction forms of an agent.

This equation makes it possible to plot a curve A, having the configuration shown in FIG. 1, which expresses the dependence of the redox potential $\phi$ along the axis of ordinates on the relationship of the activity between the oxidized and reduced forms of an agent $\alpha$ along the axis of abscissas.

Under steady conditions, i.e. under the conditions of an energy exchange with a neutral surrounding medium, which are very slowly changing in time, the redox potential of a drilling mud acquires an equilibrium value corresponding to the relationship $a_{ox}/a_{red}=0.5$. Such an important factor characterizing the chemical activity of a system as the pH also acquires, under these conditions, a neutral value equal to 7.

Any variation of these two characteristics with respect to the equilibrium state means that the system is unstable energy-wise and oxidation-reduction reactions may occur therein both when the system is in contact with the surrounding medium (wall rock, fluids getting in the drilling mud in the process of drilling) and between the particles and phases of the system proper. To resist an adverse effect of the surrounding medium in the process of drilling, the drilling mud must possess an excessive internal energy in order to compensate for this effect without any appreciable variation in the equilibrium state of the system which may have a definte range of values $a_{ox}/a_{red}=\alpha_2-\alpha_1$ (see FIG. 1) and a corresponding range of the redox potential values $(\phi_2-\phi_1)$.

The less the changes in redox potential of the system under the action of one and the same variation (intensification) of the effect of destructive factors (temperature, concentration of electrolytes), the more stable is the system.

From this it follows that by measuring the difference of the redox potential of a drilling mud before and after the effect causing degradation of the drilling mud and by correlating this difference with a quantitative measure of the exerted effect, it becomes possible to determine the capability of a system to resist this effect.

A number of experimental investigations carried out by the inventors to find out a quantitative measure of stability, salt tolerance and thermal resistance of drilling muds have resulted in deriving a number of electrical relationships. These are:

For stability:

$$C_o=(\Delta\phi/\Delta\tau)(mV/h)$$

where:

$\Delta\phi$ is the value of a difference of the redox potentials of a portion of drilling mud, mV;

$\Delta\tau$ is the time interval between measurements of the redox potential, h stands for hours.

For thermal resistance:

$$C_t=(\Delta\phi/\Delta\tau)(mV/deg)$$

where:

$\Delta\phi$ is the value of a difference of the redox potentials of a portion of drilling mud having different temperatures, mV stands for millivolts.

$\Delta t$ is the difference of temperatures of a portion of drilling mud, deg K.

For salt tolerance:

$$C_m=\Delta\phi/\Delta N, mV1/g\cdot mol$$

where:

$\Delta\phi$ is the difference of redox potentials of a portion of drilling mud with a different degree of mineralization, mV;

$\Delta N$ is the difference of concentration of dissolved salts, g·mol/l.

All these indices $C_o$, $C_t$ and $C_m$ characterize the stability of a system which is to be understood as the absence of redistribution of charges between the particles and phases of the system, but not an additive variation in the content of charged particles.

Figure 2:
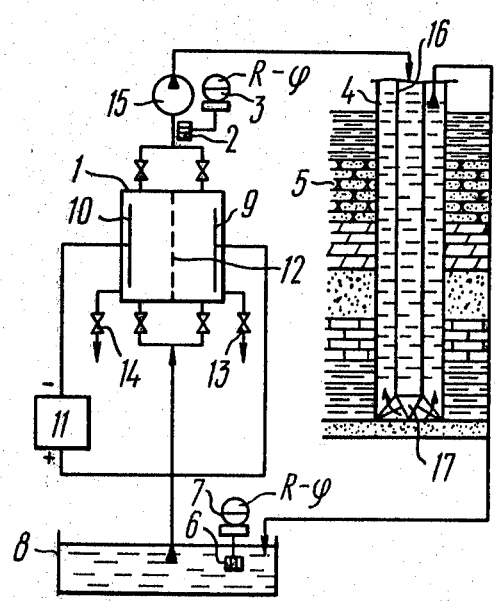
FIG. 2 illustrates a diagram for practicing the method of maintaining preset parameters of a drilling mud.

Refer now to FIG. 2.

A stable drilling mud having a value of the redox potential corresponding to the optimum parameters thereof is prepared in a vessel 1. Optimum condition of the drilling mud is obtained by common methods of control, for example, by the introduction of chemical agents and is measured by means of a redox potential sensor 2, for example, by a Krjukov's calomel electrode in the flow lines from vessel 1. Readings of the sensor 2 are registered by a secondary instrument 3. When circulating in a well 4 the drilling mud interacts physically and chemically with a rock 5 which surrounds the bore of the well 4 and has a very diversified lithologomineralogical composition. In addition, the temperature of a surrounding medium varies with increase in the depth of the well 4. All this, i.e. the chemical and temperature attack, changes the redox potential of the drilling mud, thereby varying either the oxidation or the reduction activity, i.e. brings the drilling mud out of the equilibrium state.

If the system is out of equilibrium during a long period of time, it may lead to irreversible consequences which will require substantial extra expenses to bring the drilling mud to equilibrium and to maintain the preset parameters and condition of the drilling mud. For example, if the redox potential deviates toward an increase of reducing properties, a drilled-out small-fraction clay phase upon getting into such a drilling mud starts to disperse actively due to a peptizing action of the dispersing medium possessing a high reduction potential. To rid the drilling mud of an excessive solid phase which sharply changes the rheological properties of the drilling mud, extra expenses are required for mud cleaning.

If a high oxidation potential prevails in the drilling mud, it may lead to coagulation of the system in which case to restore the system properties it would be necessary to introduce a great amount of chemical agents or, if the coagulation process has become irreversible, to replace the drilling mud. This is most frequently resorted to in drilling practice.

Deviation of the redox potential of the drilling mud flowing out of the well 4 is checked by means of a sensor 6 disposed in an intake vessel 8, and a secondary instrument 7.

To bring the system (drilling mud) to equilibrium, the drilling mud is directed from the vessel 8 into the vessel 1 wherein are installed a positive electrode 9 and a negative electrode 10 connected to a direct current supply source 11. A semi-permeable membrane 12 serves to prevent getting of the products of acid reactions from the zone of the positive electrode 9 into the zone of the negative electrode 10, and vice versa.

In case of any variation in the content of oxidation reaction products registered by the sensor 6 at the outlet of the well 4, the drilling mud flowing out of the well 4 is delivered to the vessel 1 into the zone of the negative electrode 10, i.e. the drilling mud is subjected to a unipolar electric treatment. As a result, the drilling mud acquires electrons it lost and restores the preset redox potential which is registered by the sensor 2.

The products of acid reactions formed in the zone of the positive electrode 9 (1–2 percent of the total volume of drilling mud) are discharged through a valve 13.

In case of any variation of reduction reaction products, the drilling mud flowing out of the well 4 is delivered to the vessel 1 into the zone of the positive electrode 9 wherein the content of oxidation reaction products is increased until the value of the preset redox potential is restored.

The reduction reaction products formed in the zone of the negative electrode 10 are discharged through a valve 14.

Thus, the unipolar electric treatment of a drilling mud in the zone of one of the electrodes makes it possible to quickly restore the equilibrium state of the drilling mud in the vessel 1 and to inject the mud into the well 4 by means of a pump 15 through a drilling string 16 provided with a drilling bit 17, thereby preventing any irreversible chemical reactions in the drilling mud which otherwise would have caused not only unjustified expenses but also emergency conditions and troubles in the well due to the disturbed physicochemical equilibrium between the drilling mud and wall rocks.

INDUSTRIAL APPLICABILITY

Carrying out the invention into effect makes it possible to:

reduce the consumption of chemical agents, required for restoring the properties and condition of a drilling mud, by 50–60 percent;

minimize the possibility of emergency conditions due to thermal and salt aggression and disturbed stability of well bore walls, by 35–40 percent; and, increase the quality of the drilling mud.

What is claimed is:

1. A method of maintaining the preset parameters of a drilling mud during drilling of a well comprising:

continuously measuring the redox potential of said mud at the inlet and outlet of said well;

comparing the measurements thus obtained; and registering any variation between said redox potential at said inlet and at said outlet and where a variation in the content of oxidation products is noted at said outlet;

subjecting said mud to a unipolar electric treatment at said inlet and increasing the content of reduction products in said mud and where a variation in the content of reduction products is observed at said well outlet;

subjecting said mud to a unipolar electric treatment at said inlet and increasing the content of oxidation products in said mud until the preset value of said redox potential of said mud is restored at said well outlet.

2. The method of claim 1, wherein a variation in the content of oxidation products having been detected in the mud at said outlet of said well, mud flowing from said well is subjected to said unipolar treatment in the zone of a negative electrode connected to a source of direct current.

3. The method of claim 1, wherein a variation in content of reduction products having been noted in said mud, said mud is passed into a zone of a positive electrode connected to a source of direct current wherein said content is increased until the value of the preset redox potential is restored.

* * * * *